(12) United States Patent
Zerbe et al.

(10) Patent No.: US 7,674,479 B2
(45) Date of Patent: Mar. 9, 2010

(54) SUSTAINED-RELEASE BUPROPION AND BUPROPION/MECAMYLAMINE TABLETS

(75) Inventors: Horst G. Zerbe, Hudson (CA); Nadine Paiement, Montreal (CA)

(73) Assignee: Intelgenx Corp., St. Laurent (CA)

( * ) Notice: Subject to any disclaimer, the term of this patent is extended or adjusted under 35 U.S.C. 154(b) by 395 days.

(21) Appl. No.: 11/828,287

(22) Filed: Jul. 25, 2007

(65) Prior Publication Data

US 2008/0031948 A1 Feb. 7, 2008

Related U.S. Application Data

(60) Provisional application No. 60/833,154, filed on Jul. 25, 2006.

(51) Int. Cl.
*A61K 9/20* (2006.01)

(52) U.S. Cl. .................................................... 424/464

(58) Field of Classification Search ................ 424/464, 424/471
See application file for complete search history.

(56) References Cited

U.S. PATENT DOCUMENTS

| | | | |
|---|---|---|---|
| 3,819,706 A | 6/1974 | Mehta | |
| RE33,994 E | 7/1992 | Baker et al. | |
| 5,358,970 A | 10/1994 | Ruff et al. | |
| 5,427,798 A | 6/1995 | Ludwig et al. | |
| 5,541,231 A | 7/1996 | Ruff et al. | |
| 5,731,000 A | 3/1998 | Ruff et al. | |
| 5,763,493 A | 6/1998 | Ruff et al. | |
| 5,968,553 A | 10/1999 | Maitra et al. | |
| 6,033,686 A | 3/2000 | Seth | |
| 6,096,341 A | 8/2000 | Seth | |
| 6,120,803 A | 9/2000 | Wong et al. | |
| 6,143,327 A | 11/2000 | Seth | |
| 6,153,223 A | 11/2000 | Apelian et al. | |
| 6,162,466 A | 12/2000 | Licht et al. | |
| 6,197,827 B1 | 3/2001 | Cary | |
| 6,221,917 B1 | 4/2001 | Maitra et al. | |
| 6,242,496 B1 | 6/2001 | Kulkarni et al. | |
| 6,270,805 B1 | 8/2001 | Chen et al. | |
| 6,306,436 B1 | 10/2001 | Chungi et al. | |
| 6,333,332 B1 | 12/2001 | Han et al. | |
| 6,342,249 B1 | 1/2002 | Wong et al. | |
| 6,368,626 B1 | 4/2002 | Bhatt et al. | |
| 6,462,237 B1 | 10/2002 | Gidwani et al. | |
| 6,482,987 B2 | 11/2002 | Kulkarni et al. | |
| 6,500,459 B1 | 12/2002 | Chhabra et al. | |
| 6,548,083 B1 | 4/2003 | Wong et al. | |
| 6,652,882 B1 | 11/2003 | Odidi et al. | |
| 6,723,358 B1 | 4/2004 | van Lengerich | |
| 6,780,871 B2 | 8/2004 | Glick et al. | |
| 6,797,283 B1 | 9/2004 | Edgren et al. | |
| 6,855,334 B2 | 2/2005 | Bhatt et al. | |
| 6,893,660 B2 | 5/2005 | Li et al. | |
| 6,905,708 B2 | 6/2005 | Li et al. | |
| 7,201,923 B1 | 4/2007 | van Lengerich | |
| 2002/0048600 A1 | 4/2002 | Bhatt et al. | |
| 2003/0044462 A1 | 3/2003 | Subramanian et al. | |
| 2003/0054031 A1 | 3/2003 | Li et al. | |
| 2003/0161874 A1 | 8/2003 | Li et al. | |
| 2004/0037883 A1 | 2/2004 | Zhou et al. | |
| 2004/0044005 A1* | 3/2004 | Cary | 514/253.04 |
| 2004/0228915 A1* | 11/2004 | Noack et al. | 424/471 |
| 2005/0214371 A1 | 9/2005 | Di Capua et al. | |
| 2005/0232990 A1 | 10/2005 | Boehm et al. | |
| 2005/0250838 A1 | 11/2005 | Challapalli et al. | |
| 2005/0266072 A1 | 12/2005 | Oshlack et al. | |
| 2006/0020040 A1 | 1/2006 | Chawla et al. | |
| 2006/0099260 A1 | 5/2006 | Chow et al. | |
| 2006/0165779 A1 | 7/2006 | Chawla et al. | |

FOREIGN PATENT DOCUMENTS

| | | |
|---|---|---|
| EP | 1 020 184 A1 | 7/2000 |
| WO | WO/0180824 | 11/2001 |
| WO | WO/03086362 | 10/2003 |
| WO | WO/2004/110422 | 12/2004 |

OTHER PUBLICATIONS

Pub. No. 2005/0112198 A1; Pub. Date: May 26, 2005; Inventor: Challapalli et al.

* cited by examiner

*Primary Examiner*—Michael G. Hartley
*Assistant Examiner*—James W. Rogers
(74) *Attorney, Agent, or Firm*—Price, Heneveld, Cooper, DeWitt & Litton, LLP

(57) ABSTRACT

Sustained-release bupropion hydrochloride pharmaceutical tablets and combination sustained-release bupropion hydrochloride/mecamylamine hydrochloride pharmaceutical tablets are obtained by granulating the bupropion hydrochloride with a hydroxyalkylcelluose, and blending the resulting granules within an extragranular phase composed of a particulate material that provides a sustained-release matrix, and compressing the blend into a tablet form, which then is coated, with a means to provide delayed release, such as with an enteric coating composition. The mecamylamine hydrochloride can be contained in a second granule comprising a hydroxyalkylcellulose.

10 Claims, No Drawings

SUSTAINED-RELEASE BUPROPION AND BUPROPION/MECAMYLAMINE TABLETS

CROSS-REFERENCE TO RELATED APPLICATION

This application claims priority under 35 U.S.C. §119(e) on U.S. Provisional Application No. 60/833,154 entitled STABILIZED SUSTAINED-RELEASE BUPROPION AND BUPROPION/MECAMYLAMINE TABLETS, filed Jul. 25, 2006, the entire disclosure of which is incorporated herein by reference.

FIELD OF THE INVENTION

This invention relates to pharmaceutical dosage forms, and more specifically to sustained release tablets, and particularly to sustained-release bupropion hydrochloride tablets.

BACKGROUND

Bupropion is used as an antidepressant. It has also been used either alone or in combination with other drugs as a smoking cessation aid. Bupropion hydrochloride is stable by itself under normal storage conditions, but can degrade in the presence of certain conventional excipients used in commercial formulations. It has been theorized that small amounts of impurities in the excipients, typically residual impurities such as peroxides, superoxides, hypochlorites and formic acid introduced during the manufacturing processes, can interact with the bupropion hydrochloride to cause decomposition during storage. Accordingly, it has been proposed that one possible strategy to eliminate or reduce decomposition of bupropion hydrochloride in pharmaceutical dosage forms is to pretreat the excipients to remove or neutralize impurities that can induce oxidation, add chelating agents to formulations to prevent metal induced oxidation, and/or add antioxidants such as L-cysteine hydrochloride to pharmaceutical dosage forms containing bupropion hydrochloride.

Commercially available sustained-release oral formulations of bupropion hydrochloride have been prepared by mixing the bupropion hydrochloride with a stabilizing agent and with various celluloses, alkyl celluloses and hydroxyalkylcelluloses, carboxyalkylcelluloses, polyalkylene glycols and acrylic acid polymers.

The utility of pharmaceutical therapies and compositions involving the combination of mecamylamine hydrochloride and bupropion hydrochloride in the treatment of tobacco addiction or nicotine addiction, for palliating nicotine withdrawal symptoms, and/or facilitating smoking sensation is disclosed in U.S. Pat. No. 6,197,827, which is incorporated by reference in its entirety herein. This patent generally describes the concept of administering mecamylamine and bupropion, either individually or in a single tablet, but does not disclose any particular formulation, or provide details as to how stable sustained-release tablet formulations comprising a therapeutically effective combination of mecamylamine hydrochloride and bupropion hydrochloride can be prepared. There is only a relatively general suggestion that time-release formulations may be prepared "as is known in the art and disclosed in U.S. Pat. Nos. 4,690,825 and 5,005,300," and that "conventional means with pharmaceutically acceptable excipients such as binding agents . . . ; fillers . . . ; disintegrants . . . ; or wetting agents . . . ; glidants, artificial and natural flavors and sweeteners; artificial or natural colors and dyes; and stabilizers" may be employed. This teaching does not recognize potential interactions between mecamylamine hydrochloride and bupropion hydrochloride.

SUMMARY

In accordance with an aspect of this invention, an alternative solution to providing sustained release of bupropion hydrochloride in a tablet dosage form is provided. In accordance with this aspect of the invention, a sustained-release bupropion hydrochloride granulation is distributed in a sustained-release matrix. More particularly, the pharmaceutical tablets in accordance with this aspect of the invention comprise a granular phase composed of bupropion hydrochloride and a hydroxyalkylcellulose. The granular phase is distributed within an extragranular phase comprising a particulate material that provides a sustained-release effect, such as by providing a diffusion barrier and/or controlled erosion. The formed tablet optionally then is provided with a means to obtain a delayed release of active, such as, an enteric coating.

In accordance with a related aspect of the invention, a sustained release bupropion hydrochloride pharmaceutical tablet is prepared by granulating bupropion hydrochloride with a hydroxyalkylcellulose in a wet granulation process. The resulting granulation is dried to an acceptable moisture content, and the dried granulation may optionally be milled and/or screened to achieve a desired granulation particle size. Thereafter, the dried granulation is dry blended with a particulate material capable of forming a sustained-release matrix in which the bupropion hydrochloride granules are distributed. The resulting blend is then compressed into a tablet form. Optionally, the tablet can be provided with a means for obtaining delayed release, such as, an enteric coating.

In accordance with another aspect of the invention, there is provided a single tablet dosage form providing sustained release of both bupropion hydrochloride and mecamylamine hydrochloride in which the bupropion hydrochloride and mecamylamine hydrochloride are configured to minimize or remove interactions with each other. More particularly, the invention provides a combination sustained-release bupropion hydrochloride, sustained-release mecamylamine pharmaceutical tablet in which mecamylamine hydrochloride and bupropion hydrochloride granulation are distributed in an extragranular phase comprising a particulate material capable of providing a sustained-release matrix. The tablet can have an optional means to obtain delayed release of the active, such as, an enteric coating.

In accordance with a related aspect of the invention, a combination sustained-release bupropion hydrochloride, sustained-release mecamylamine hydrochloride pharmaceutical tablet is prepared by granulating bupropion hydrochloride with a hydroxyalkylcellulose; drying the bupropion hydrochloride granulation; optionally milling and/or screening the dried granulation; dry blending the dried granulation with mecamylamine hydrochloride or mecamylamine hydrochloride granules made in the same fashion as the bupropion granules; blending the combined granulations of bupropion and mecamylamine with a suitable extragranular external phase comprising a particulate material; and compressing the resulting blend into a tablet form. The tableted form may optionally contain a means for obtaining delayed release, such as an enteric coating.

These and other features, advantages and objects of the present invention will be further understood and appreciated by those skilled in the art by reference to the following specification and claims.

DETAILED DESCRIPTION

In accordance with the various embodiments of the invention, bupropion hydrochloride is incorporated in a granular phase that is distributed within an extragranular phase which together provides a sustained release matrix for the bupropion hydrochloride (Alternative forms of bupropion can be used, such as, the free base. For the purposes of the instant invention, all pharmacologically active forms of bupropion are usable and are included in the term, "bupropion hydrochloride or bupropion.) The tablet form optionally is provided with a means for obtaining delayed release of the active, such as, an enteric coating to achieve a further delayed and sustained dissolution profile, as well as a shelf stable pharmaceutical form. Conventional wet granulation techniques may be employed for preparing the bupropion hydrochloride granules. The terms "granule", "granulation" and "granular phase" refer to particulate agglomerates or aggregates formed by combining the components of the granulation in the presence of a suitable liquid to bind individual particles into aggregated clumps or clusters comprising the individual components of the granulation. Depending on the granulation techniques employed, the selected ingredients, and the desired release properties, the granules, after being dried, can be milled and/or sieved to achieve a desired granule size.

Preferably, bupropion hydrochloride is granulated in a manner that maintains the pharmacologic activity of the bupropion hydrochloride. Hence, a suitable liquid used in the wet granulation process is one which is not detrimental to any component of the tablet of interest. Hence, the liquid can be one which contains suitable buffering compounds, for example. A suitable liquid is one which can be adjusted at a basic or acidic pH that enables the formation of the granules while maintaining pharmacologic activity of the bupropion. For example, acidic conditions can favored for use with bupropion hydrochloride because of the ionic state of that molecule, whereas basic conditions are favored for use with the free base (Husa's Pharmaceutical Dispensing, Martin, ed., Mack, Easton, Pa., $6^{th}$ ed., 1966). Thus, the water for the wet granulation process can be acidified at a suitable pH for the wet granulation of the bupropion hydrochloride salt and the hydroxyalkylcellulose. In general, suitable acids include those that lower the pH of an aqueous solution to a value in the range from about 0.5 to about 4.0 when added to the neutral solution at a concentration of about 0.003 parts by weight to about 100 parts by weight of the solution. An example of a suitable acidic neutralizer for bupropion hydrochloride is an inorganic acid, such as, hydrochloric acid, although the common ion effect of using HCl with the hydrochloride salt of bupropion may be considered.

The term "therapeutically effective amount" refers to an amount of a pharmaceutically active agent, which when administered to a particular subject, considering the subject's age, weight and other relevant characteristics, will attenuate, ameliorate, or eliminate one or more symptoms of a disease or condition that is treatable with the pharmaceutically active agent. Generally, the therapeutically effective amount of bupropion is provided in the commercially available products, and that of mecamylamine is provided in.

For the purposes of the instant invention, "about" is meant to mean a range of no more than 5% about the stated amount, value or figure, that is the range comprises 5% less than the stated amount, value or figure to 5% more than the stated amount, value or figure.

By "active" is meant a pharmacologically active compound, such as bupropion hydrochloride or mecamylamine hydrochloride.

Suitable hydroxyalkylcellulose polymers that may be employed for preparing the bupropion hydrochloride granulation include hydroxymethycellulose, hydroxyethylcellulose, and hydroxypropylcellulose.

The amount of bupropion hydrochloride is preferably adjusted to provide conventional therapeutic amounts in the range from about 25 milligrams to about 500 milligrams, such as 50, 75, 100, 125, 150, 175, 200, 225, 250, 275, 300, 325, 350, 375, 400, 425, 450, 475 and 500 milligrams. Larger doses of bupropion, despite formulation size, are contemplated.

Surprisingly, the amount of hydroxyalkylcellulose needed in the bupropion hydrochloride granules to achieve effective sustained release of the bupropion hydrochloride in the tablet dosage forms of the invention, and to prevent degradative interactions between bupropion hydrochloride and mecamylamine hydrochloride for tablets containing these two pharmaceutically active compounds, is relatively low. Typically, a suitable and effective amount of hydroxyalkylcellulose in the granular phase is from about 10 to about 30% by weight of the granular phase, with the remaining about 70% to about 90% of the weight of the granular phase being primarily bupropion hydrochloride. The preferred hydroxyalkylcellulose is hydroxypropylcellulose. The granules can contain other inert excipients as a design choice, such as a lubricant, a glidant and so on.

For the sustained-release bupropion hydrochloride tablets which do not contain mecamylamine hydrochloride, the relative amount of granular phase to extragranular phase may vary considerably, depending on the selected tablet dose and the desired release properties. However, the granular phase typically and generally preferably comprises about 30% to about 70% of the combined weight of the granular phase and the extragranular phase. In the case of tablets providing both sustained release of bupropion hydrochloride and mecamylamine hydrochloride, the mecamylamine need not, but is preferably granulated with a hydroxyalkylcellulose, preferably hydroxypropylcellulose, to effectively reduce or eliminate potential interactions between bupropion hydrochloride and mecamylamine hydrochloride in the tablet. However, because pharmaceutically effective doses of mecamylamine hydrochloride are substantially lower than those of bupropion hydrochloride, the total amount of bupropion hydrochloride granules and mecamylamine hydrochloride granules (when mecamylamine hydrochloride is incorporated into the dosage form in a granular phase) is in a range of from about 30% to about 75% of the combined weight of the two granular phases and the extragranular phase.

Therapeutically effective amounts of mecamylamine hydrochloride are well known in the art, and generally range from about 1 to about 10 milligrams per tablet, with specific examples being 2, 3, 4, 5, 6, 7, 8 and 9 milligrams. Higher doses of mecamylamine hydrochloride are contemplated as the need may command.

The external phase may be comprised of generally any particulate material that can be compressed into a tablet form and that provides a sustained-release matrix. Materials having suitable sustained-release properties are generally well known in the art, and typically provide sustained release by providing a diffusion barrier for the active or active ingredients and/or by eroding at a desired controlled rate, with the result being a relatively uniform or constant rate of release of the active ingredient or active ingredients over an extended period of time, such as about 4, about 8, about 16 or about 24 hours. Such sustained release is desirable for maintaining therapeutically effective blood plasma levels of the drug over an extended period of time without requiring administration of multiple tablets over the extended period. Examples of suitable extragranular particulate materials that may be used for providing a sustained-release matrix include poly(vinylacetate), polyvinylpyrrolidone, blends of poly(vinylacetate) and polyvinylpyrrolidione, copolymers of vinylpyrrolidone such as copolymers of vinylacetate and vinylpyrrolidone, polyethylene oxides, modified starches, and hydroxyethylcellulose.

The external phase may also contain small amounts of conventional additives such as colorants, opacifiers, glidants, etc.

Suitable extragranular excipients include water-swellable and/or water-erodible polymers, with suitable and preferred examples including polyvinylpyrrolidone, poly(vinylacetate), copolymers of vinylpyrrolidone and vinylacetate and blends thereof. Also desirable are blends further comprising a polyalkylene oxide, such as polyethylene glycol or polyethylene oxide, in an amount effective to adjust the hydrophilicity of the sustained release matrix provided by the extragranular phase, and thereby adjust the rate of sustained release.

The extragranular phase may contain other excipients, such as a lubricant, a glidant, a colorant, a binder, a preservative and so on.

In addition to sustained release, it is desirable to provide bupropion hydrochloride and bupropion hydrochloride/mecamylamine hydrochloride tablet dosage forms having delayed-release properties. The term "delayed release" as used herein refers to release of the pharmaceutically active compound or compounds that is delayed until after the dosage form has passed through the stomach and into the intestine. As is well known in the art, such delayed-release can be achieved by coating the compressed tablet with a polymer coating composition that remains intact in the upper part of the gastrointestinal tract while in contact with acidic gastric fluids, but which readily decomposes or solubilizes at the higher pH in the intestine. An example of such a polymer coating is an enteric coating. Enteric coatings are known, for example, see, U.S. Pat. Nos. 5,888,550; 6,139,875; 6,420,473; and 6,455,052. Examples of delayed release compositions can be found in U.S. Pat. Nos. 5,108,758 and 5,151,273.

An enteric coating generally comprises components soluble in a liquid at a pH 5 or more and includes components that impart resistance to gastric conditions, as known in the art. Some examples of the components for an enteric coating include anionic acrylic resins, such as methacrylic acid/methyl acrylate copolymer and methacrylic acid/ethyl acrylate copolymer (for example, Eudragit L, Eudragit S (Rohm, Germany), hydroxypropylmethylcellulose acetate succinate, hydroxypropylmethylcellulose phthalate, cellulose acetate phtalate, carboxymethylcellulose acetate phthalate, shellac and so forth. Mixtures of those compounds also may be used. The enteric coating can comprise from about 1% to about 10% or more of the combined weight of the tablet, depending on the components used in the coating. For example, the enteric coating can comprise about 5%, about 6%, about 7%, about 8%, about 9%, about 10%, about 11%, about 12% or more of the combined weight of the tablet. The enteric coating is selected to provide a desired delayed release of the active to achieve the desired dissolution profile. The composition of the coating and/or the thickness of that coating on the tablet can influence the useful shelf life of the product.

Other auxiliary coating aids such as a minor amount of a plasticizer, such as acetyltributylcitrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol, propylene glycol and mixtures thereof in combination with an antisticking agent which may be a silicate such as talc, can be used. Titanium oxide also can be included in the coating, as well as known cellulosic materials. A flavorant or colorant may be included. The components may be added to the methacrylic acid copolymer in combination with appropriate solvents.

The delayed release enteric coating generally can be one which causes a delay of active dissolution, for example, active release from the tablet will not substantially occur until after the dosage form is removed from a simulated gastric fluid in vitro or the stomach in vivo. Essentially, the enteric coating is one which does not dissolve under conditions found in the stomach but dissolves under conditions found in the intestine, for example, based on the acidity of the environment. It is also noted that the enteric coating and the thickness thereof contribute to the shelf life of the active(s) in the tablet form of interest.

It may be beneficial to incorporate a lubricant in the extragranular phase to aid tableting. While common tableting lubricants such as magnesium stearate may be employed, it has been discovered that stearic acid, in addition to providing the desired lubricating effect, also imparts enhanced storage stability to the resulting tablets.

The following examples are illustrative of the invention, but do not define the limits of the invention.

EXAMPLE 1

Examples of formulations for sustained-release bupropion hydrochloride tablets and bupropion hydrochloride/mecamylamine hydrochloride tablets are summarized in the following table. The tablets were made using a wet granulation method where 0.3N HCl was used as the granulation liquid. The active and HPC were homogenized for two minutes in a high shear mixer. The mixer was set at 500 rpm and the chopper motor was set at 1000 rpm. The bupropion wet granules were air dried briefly and then passed through a 2.36 mm sieve and then through a 1.18 mm sieve. The wet granulation of mecamylamine was performed with water. The mecamylamine wet granules were dried overnight at 50° C. and then passed through a 1.18 mm sieve. The one or two granules were blended and then mixed with Kollidon SR and polyethylene oxide previously passed through a 0.60 mm sieve. All excipients were blended for 5 minutes in a V blender. Following the addition of lubricant and other excipients, blending was continued for another minute. The tablet was compressed on a rotary press. The tablets were coated using a solution containing sodium carboxymethyl cellulose, Eudragit L30D-55, PEG 8000, talc and titanium dioxide. The coating was applied using a fluid bed drier at a temperature of 40° C. at 0.8 bar, with a flow rate of 2.5 g/min, to provide a weight gain of 4%. The illustrated exemplary tablet formulations (1-5) prevent potential interactions between bupropion hydrochloride and mecamylamine hydrochloride for those tablets containing both active ingredients in a single tablet dosage form. The tablet were stable, which means that at least 80% of the initial potency of the bupropion hydrochloride in each tablet was maintained after storage for at least 10 weeks at 40° C. and 75% relative humidity.

TABLE

Bupropion/Mecamylamine Formulation

| Dosage Bupropion/ Mecamylamine (mg) Weight (mg per tablet) | 1 | 2 | 3 | 4 | 5 |
|---|---|---|---|---|---|
| Active Granulations: | | | | | |
| Bupropion HCl | 225.00 | 225.00 | 225.00 | 225.00 | 450.00 |
| Hydroxypropyl-cellulose (HPC) (Klucel GXF) | 40.00 | 40.00 | 40.00 | 40.00 | 80.00 |
| Mecamylamine HCl | — | 3.00 | 6.00 | 9.00 | — |
| Hydroxypropyl-cellulose (Klucel GXF) | — | 0.67 | 1.33 | 2.00 | — |
| External phase: | | | | | |
| Poly(vinylacetate) povidone blend (Kollidon SR) | 101.00 | 101.00 | 101.00 | 101.00 | 101.00 |
| Polyethylene oxide (WSR N60K) | 58.00 | 58.00 | 58.00 | 58.00 | 58.00 |
| Stearic acid | 7.50 | 7.50 | 7.50 | 7.50 | 7.50 |
| Colloidal silicon dioxide | 2.50 | 2.50 | 2.50 | 2.50 | 2.50 |
| Coating: | | | | | |
| Methacrylic acid copolymer dispersion | 10.42 | 10.50 | 10.63 | 10.68 | 16.84 |
| Talc | 4.17 | 4.20 | 4.21 | 4.27 | 6.67 |
| Polyethylene glycol 8000 | 1.39 | 1.40 | 1.40 | 1.42 | 2.22 |
| Titanium dioxide | 1.04 | 1.05 | 1.05 | 1.07 | 1.67 |
| Carboxymethyl-cellulose sodium (Hercules 7LF) | 0.35 | 0.35 | 0.35 | 0.36 | 0.56 |
| Tablet weight (mg) | 451.37 | 455.17 | 458.97 | 462.80 | 726.96 |

EXAMPLE 2

A tablet containing 225 mg of bupropion as provided in Example 1 was compared to Wellbutrin XL 150 in a dissolution study using USP 26 App. (basket) or the two paddle test for extended release tablets. In the paddle test, at 50 rpm, the tablets were exposed to two paddles in 900 ml of water for 8 hours. In the basket test, tablets were exposed to 0.1 N HCl for two hours to mimic gastric conditions. After the two hours, the tablets were moved to simulated intestinal fluid at pH 6.8 at 100 rpm for 22 hours. At one hour time points throughout the incubation in the basket or paddle tests, beginning at time 0, a fluid sample was obtained and tested for presence and amount of bupropion. Simulated intestinal fluid (SIF) can comprise a Tris buffer (0.05 M Tris adjusted to pH 6.8 with 2 N NaOH).

Throughout the 24 hour period, at the 24 hour time point, all tablets had released about 95% of the bupropion dose contained in the tablet, the tablet of the instant invention released nearly the same percentage of bupropion as did the name brand product, including a two hour lag at the onset wherein essentially no bupropion was released from the tablets.

The same results were obtained with tablets containing 450 mg of bupropion. In one set of experiments, some tablets did not contain an enteric coating. That tablet released about 45% of the carried bupropion at the two hour time point, and about 70% at the four hour time point. In another set of experiments, two other tablets with 450 mg of bupropion contained a 4.68% enteric coating. One tablet also included a lubricant, magnesium stearate, in the formulation. Both of those tablets demonstrated a nearly identical dissolution profile as observed for Wellbutrin XL 150. In this set of experiments, the initial two hour incubation was done not in 0.1 N HCl but in simulated gastric fluid (SGF) which comprises 12 g of sodium chloride and 42 ml of hydrochloric acid, diluted to 6 liters and pH adjusted to 1.2.

EXAMPLE 3

Stability of bupropion HCl 225 mg extended release tablets and release profile were examined. Tablets were made as described in Example 1. Tablets were then stored at two different conditions, 25° C./60% RH and 40° C./75% RH. Samples were obtained at 0 and 1 month, and for the lower temperature regimen, also at 3 months, and then tested for bupropion, content uniformity, dissolution and related compounds. The results were compared to the specification of related approved drugs.

Throughout the lower temperature regimen, the instant tablets conformed with the standard parameters. At the higher temperature regimen, the instant tablets conformed at the 0 and one month sampling periods.

EXAMPLE 4

In vitro dissolution was compared to in vivo absorption, the amounts absorbed in vivo were calculated using the Wagner/Nelson method and plotted against the amounts released in vitro at equivalent time points using a Levy plot, practicing known methods. The tablet of interest contained 225 mg of bupropion, and was compared to Wellbutrin XL 300 mg.

Selected patients screened to meet parameters established in the approved protocol at a VA hospital, were provided with a single tablet after a nine hour fast. Blood samples were obtained, serum separated and the amount of bupropion was determined by liquid chromatography and mass spectrometry. A blood sample was also take prior to administration of the tablet.

Over a 36 hour period, nearly 100% of the bupropion was absorbed. The two hour lag period was noted. Overall, the profiles were the same, with the instant tablet identical to the Wellbutrin up through six hours, and then demonstrating an absorption profile that paralleled that of Wellbutrin, although at a level about 5% lower. The Wagner/Nelson method used assumes a one compartment, one body model for the drug. On the other hand bupropion has been reported to follow a two compartment, one body model. The Lou Riegelman method provides a suitable two compartment model. Nevertheless, the Wagner/Nelson method provides a sufficiently accurate approximation of the true absorption profile.

The Levy plots were substantially identical, the data best fit a second degree polynomial relationship. Hence, the absorption of the drug is nearly quantitative during the first eight hours after administration but is reduced as the dosage from enters the lower parts of the intestine. The pattern was observed for both Wellbutrin and the instant tablet. Thus, the absorption rate is dependent on the drug and not on the dosage.

The overall amount of drug released was about 5% lower than that of Wellbutrin. However, the maximum concentration was the same and was obtained at the same time.

EXAMPLE 5

Tablets containing bupropion or bupropion and mecamylamine made as provided in Example 1 above, were enterically coated using a composition containing 39.76% of Eudragit L30 D55 (30% dispersion), 4.77% talc, 1.59% PEG 8000, 1.20% titanium dioxide, 0.4% carboxylmethyl cellulose sodium and 52.28% water. Solids comprised 20% of the solution, and polymers comprised 12% of the solution. The enteric coating was applied to the formed tablet. One set of tables contained 4% by weight of enteric coating, and another set contained a 6% by weight enteric coating. A degradation product of bupropion is m-chlorobenzoic acid, and presence of that product was used as a measure of the shelf life of the tablets of interest.

| Lot no. | % m-chlorobenzoic acid* | |
|---|---|---|
| | Finished product | Stored tablets 6 months at room temp |
| 200604/KL2B0/01, 225 (4% coating) | 0.0 | 0.1 (3 months) |
| 200604/KL2B3/01, 225/3 (4% coating) | 0.0 | 0.1 (3 months) |
| 200604/KL2B9/01, 225/9 (4% coating) | 0.0 | 0.15 (3 months) |
| 06H-BMT209-0001 225/9 (4% coating) | 0.0 | 0.3 |
| 06R-BUP200-0007 225 (6% coating) | 0.0 | 0.0 |
| 06R-BMT206-0009 225/6 (6% coating) | 0.0 | 0.0 |
| 06R-BMT209-0010 225/9 (6% coating) | 0.0 | 0.0 |
| 06R-BMT203-0008 225/3 (6% coating) | 0.0 | 0.0 |

The shelf life of bupropion tablets was enhanced by using the particular enteric coating in a higher amount. The thickness of the enteric coating has no effect on the in vivo dissolution profile.

The above description is considered that of the preferred embodiments only. Modifications of the invention will occur to those skilled in the art and to those who make or use the invention. Therefore, it is understood that the embodiments described above are merely for illustrative purposes and not intended to limit the scope of the invention, which is defined by the following claims as interpreted according to the principles of patent law, including the doctrine of equivalents.

The invention claimed is:

1. A sustained release pharmaceutical tablet comprising:
   sustained release granules consisting essentially of bupropion hydrochloride admixed with a hydroxyalkylcellulose; and
   an extragranular phase comprising a particulate material that provides a sustained release matrix; said particulate material is selected from the group consisting of polyvinylacetate, blends of polyvinylacetate and polyvinylpyrrolidone, a vinylpyrrolidone copolymer and polyethylene oxide,
   the granules being distributed within the extragranular phase.

2. The tablet of claim 1 further comprising sustained release mecamylamine hydrochloride granules.

3. The tablet of claim 1, wherein said extragranular phase further comprises mecamylamine hydrochloride.

4. The tablet of claim 1, wherein said hydroxyalkylcellulose is hydroxypropylcellulose.

5. The tablet of claim 1, further comprising an enteric coating.

6. A sustained release pharmaceutical tablet comprising:
   an uncoated sustained release granular phase comprising bupropion hydrochloride admixed with a hydroxyalkylcellulose; and
   an extragranular phase comprising a particulate material that provides a sustained release matrix; said particulate material is selected from the group consisting of polyvinylacetate, blends of polyvinylacetate and polyvinylpyrrolidone, a vinylpyrrolidone copolymer and polyethylene oxide,
   the uncoated granular phase being distributed within the extragranular phase.

7. The tablet of claim 6, further comprising sustained release mecamylamine hydrochloride granules.

8. The tablet of claim 6, wherein said extragranular phase further comprises mecamylamine hydrochloride.

9. The tablet of claim 6, wherein said hydroxyalkylcellulose is hydroxypropylcellulose.

10. The tablet of claim 6, further comprising an enteric coating.

* * * * *

UNITED STATES PATENT AND TRADEMARK OFFICE
CERTIFICATE OF CORRECTION

PATENT NO. : 7,674,479 B2  Page 1 of 1
APPLICATION NO. : 11/828287
DATED : March 9, 2010
INVENTOR(S) : Horst G. Zerbe et al.

It is certified that error appears in the above-identified patent and that said Letters Patent is hereby corrected as shown below:

Col. 1, line 17, "sustained release" should be -- sustained-release --.

Col. 1, line 50, "sensation" should be -- cessation --.

Col. 2, line 20, "sustained release" should be -- sustained-release --.

Col. 3, line 6, "sustained release" should be -- sustained-release --.

Col. 3, lines 7 and 11, "hydrochloride (Alternative . . . bupropion.)" should be -- hydrochloride. (Alternative . . . bupropion.") --.

Col. 3, line 35, "can" should be -- are --.

Col. 3, line 61, "than 5% about" should be -- than about 5% of --.

Col. 4, line 3, "hydroxymethycellulose" should be -- hydroxymethylcellulose --.

Col. 5, line 20, "sustained release" should be -- sustained-release --.

Col. 5, line 41, "delayed release" should be -- delayed-release --.

Col. 5, line 52, "phtalate" should be -- phthalate --.

Col. 6, line 11, "delayed release" should be -- delayed-release --.

Col. 6, line 64, "tablet" should be -- tablets --.

Col. 8, line 63, After "dosage" delete "from".

Col. 9, line 15, "tables" should be -- tablets --.

Signed and Sealed this

Seventh Day of September, 2010

David J. Kappos
*Director of the United States Patent and Trademark Office*